United States Patent [19]
Utsugi et al.

[11] Patent Number: 4,552,129
[45] Date of Patent: Nov. 12, 1985

[54] ENDOSCOPE

[75] Inventors: Mikio Utsugi; Tathuya Yamaguchi, both of Tokyo, Japan

[73] Assignee: Olympus Optical Co., Ltd., Tokyo, Japan

[21] Appl. No.: 519,741

[22] Filed: Aug. 2, 1983

[30] Foreign Application Priority Data

Aug. 9, 1982 [JP] Japan .................. 57-138259
Aug. 19, 1982 [JP] Japan .................. 57-143682

[51] Int. Cl.[4] ............................................. A61B 1/00
[52] U.S. Cl. .................................................. 128/4
[58] Field of Search ................................... 128/4–8

[56] References Cited

U.S. PATENT DOCUMENTS 1,627,941  5/1927  Wappler ............................ 128/7
3,294,085  12/1966  Wallace ............................ 128/6
4,078,555  3/1978  Takashi .
4,279,245  7/1981  Takagi et al. ..................... 128/4
4,341,205  7/1982  Hosono et al. ................... 128/6

Primary Examiner—Edward M. Coven
Assistant Examiner—Max F. Hindenburg

[57] ABSTRACT

An endoscope includes a main body for holding an operating mechanism in place and a casing within which the main body is enclosed. The casing includes a hollow body-like casing body with one of its end portions serving to stabilize a base end of the main body and its other end portion having an opening portion permitting a protruded portion of the main body to be extended of the casing and a cylindrical gripping cover having an end portion allowed to abut against the other end portion of the casing body and covering the protruded portion of the main body. The main body includes a nut screwing engagement with an external thread of the main body and engaged with a protruded portion of the gripped cover, whereby the nut acts to urge the gripping cover toward the casing body and, at the same time, to urge the casing body toward the gripping cover, thereby pressing the end portion of the gripping cover and the other end portion of the casing body against each other.

7 Claims, 14 Drawing Figures

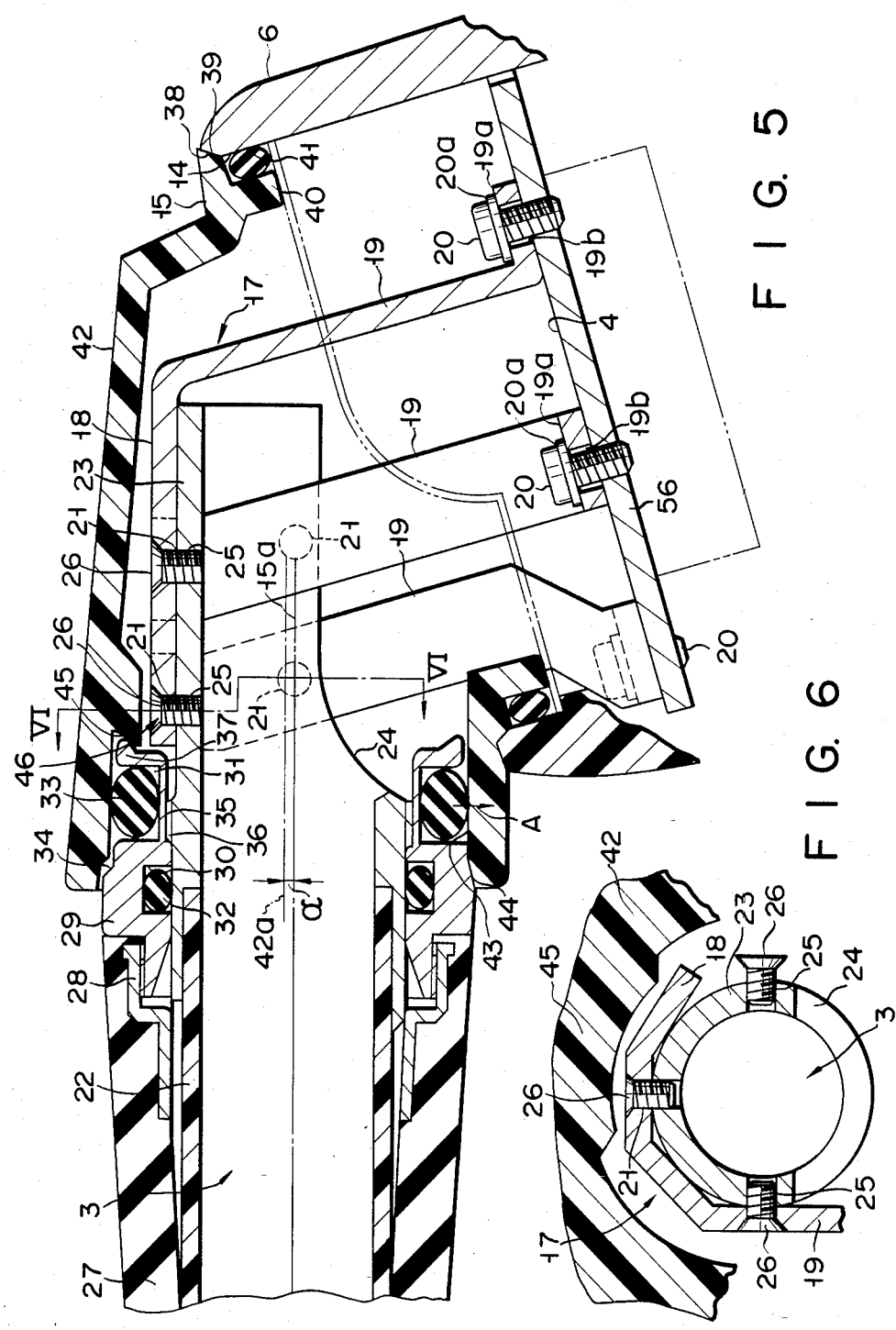

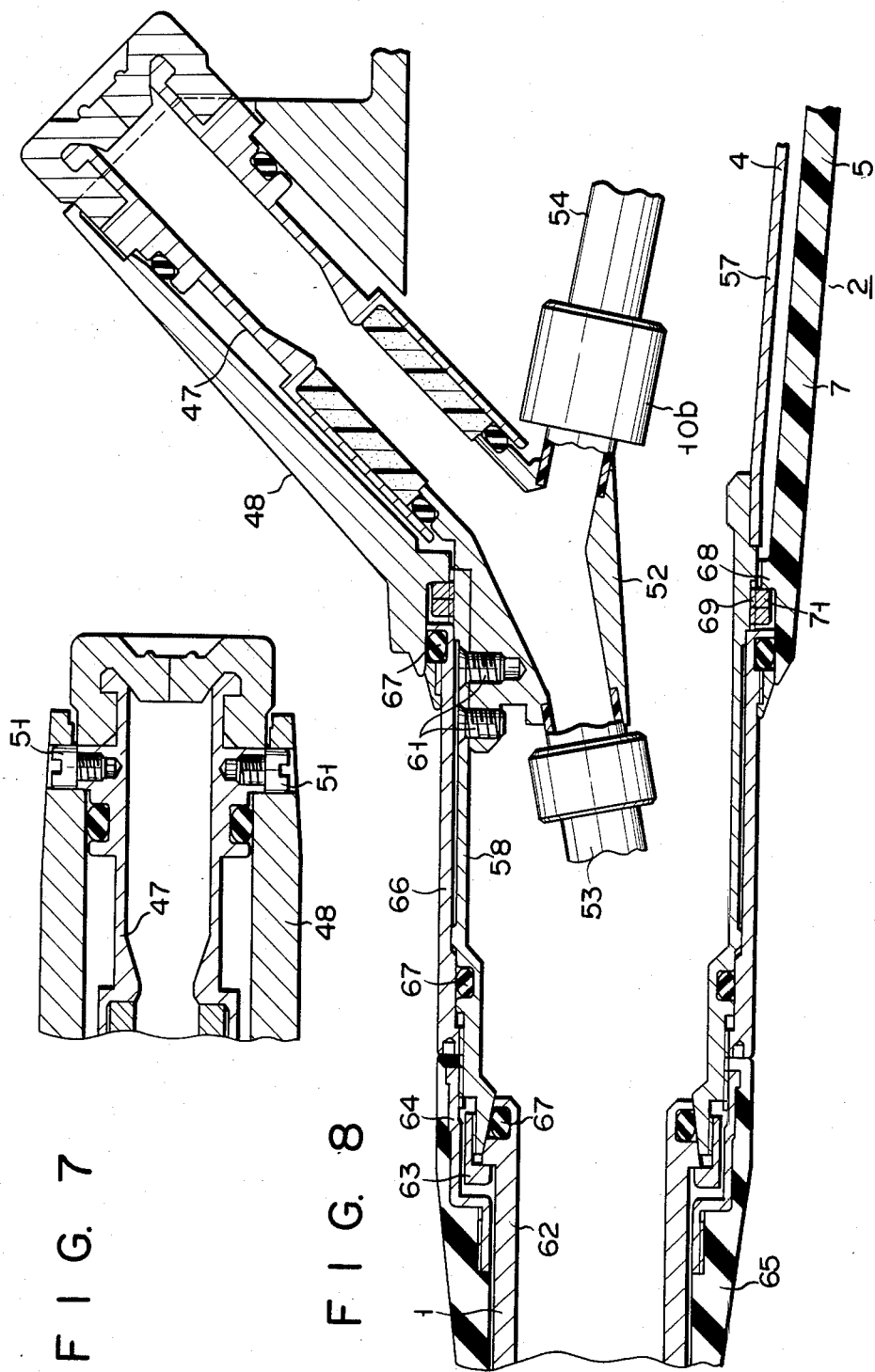

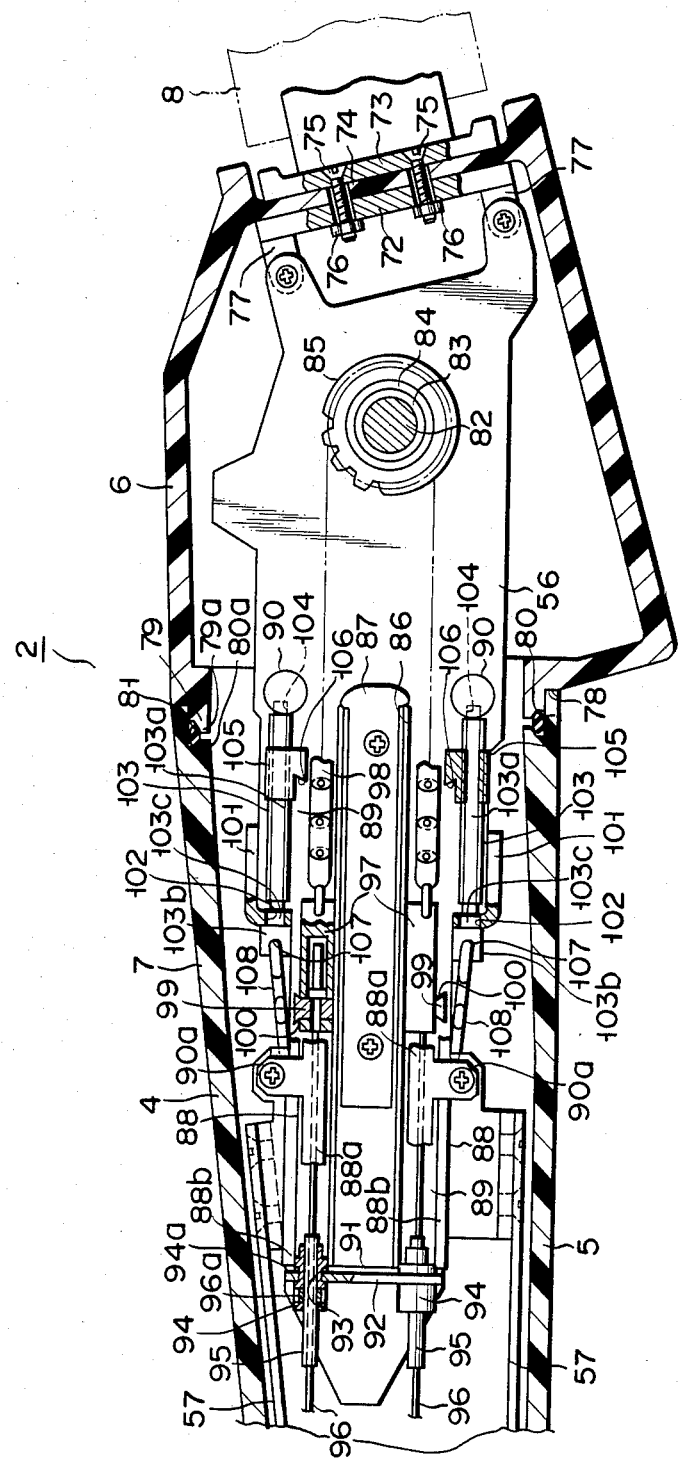

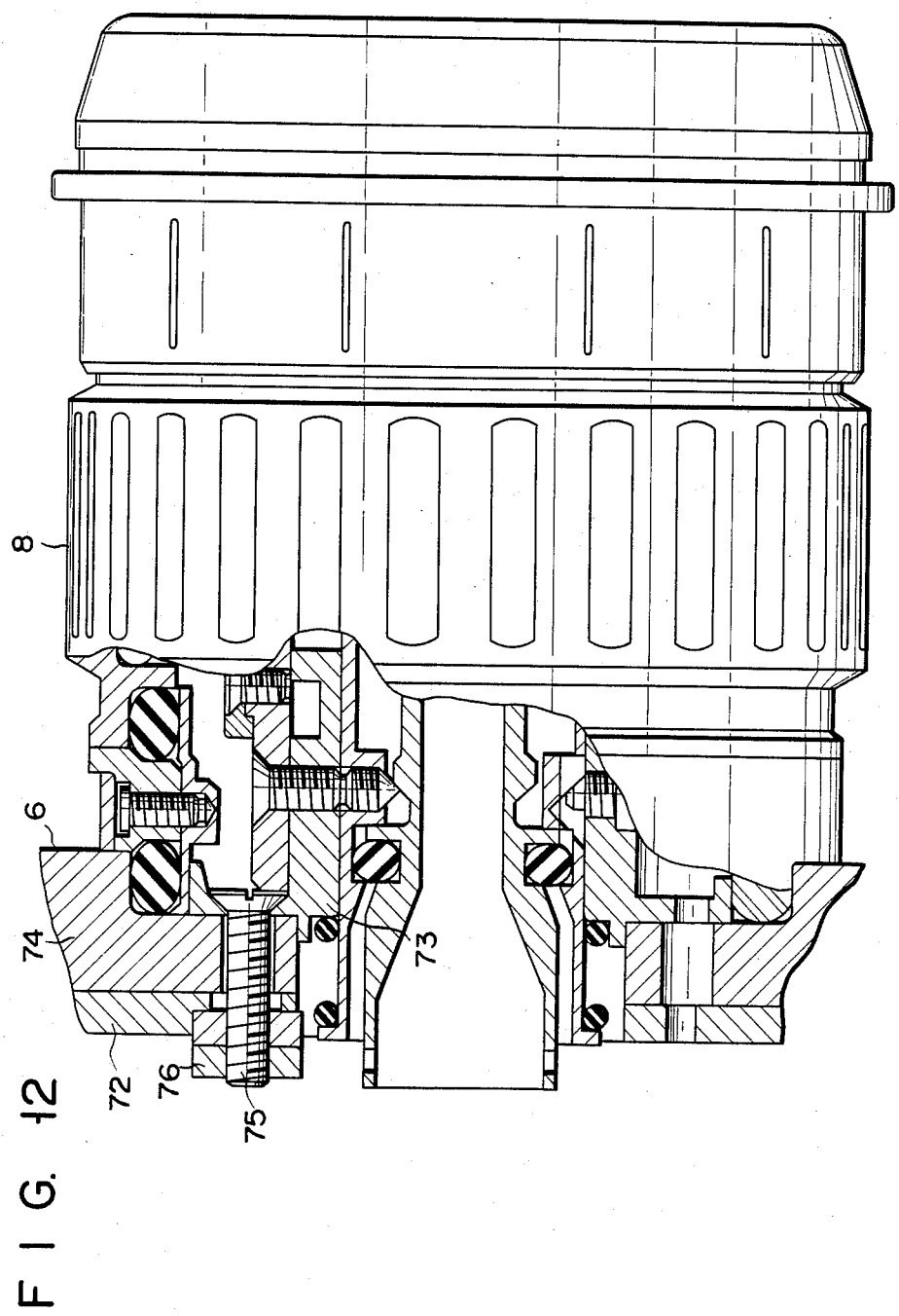

ENDOSCOPE

BACKGROUND OF THE INVENTION

The present invention relates to an endoscope having an operation section which has been structurally improved, thereby facilitating assembly of the endoscope.

The operation section of a prior art endoscope is assembled in such a way that, as shown in FIG. 1, a pair of covering members b are screwed and fastened by means of, e.g., setscrews, to a base member a serving as a main body of said operation section, from the right and left sides thereof, respectively. In this case, however, the base member a is designed to have sufficient mechanical strength and the covering members b are intended to function only as a casing attached to the base member a.

However, the base member a within the operation section has disposed therearound a plurality of built-in members c, such as a bending operation wire, a treating instrument inductor raising wire, an air/water intake tube, various channels, an electrical wire distribution, etc. Moreover, within the operation section having such a base member, the elements extended into the side of the endoscope whose base member has an insertion portion must be connected to the elements extended from the side of an ocular portion or from the side of a connector portion connected to accessory devices. For this reason, it is impossible to construct the base member a in such a way that its structure may entail a large section modulus to house the built-in members. At best only a structure such as that shown in FIG. 1, having a sectional configuration shaped like the letter I, may be adopted for the base member.

Accordingly, it was necessary to make the operation section large, both in weight and thickness, to ensure sufficient mechanical strength to resist compression and bending forces. In other words, the prior art endoscope was unsatisfactory as an endoscope which might be operated over long periods, even with one hand.

SUMMARY OF THE INVENTION

In view of the above, a primary object of the present invention is to provide an endoscope with a structure having sufficient mechanical strength, while satisfying the requirement that the operation section be light and small, a prerequisite of the operation section of an endoscope operable with one hand over a long period of time.

BRIEF DESCRIPTION OF THE DRAWINGS

FIGS. 2 to 14 show the endoscope according to an embodiment of the invention, in which:

FIG. 2 is a perspective view schematically showing the endoscope as a whole;

FIGS. 3 and 4 are perspective views of a main body of the operation section from different directions;

FIG. 5 is a sectional view showing a portion of a structure wherein a light guide cable is connected to the operation section;

FIG. 6 is a sectional view taken along line VI—VI of FIG. 5;

FIG. 7 is a sectional view showing a joining portion of a channel mouth;

FIG. 8 is a sectional view showing a joining portion between the operation section and insertion section of the endoscope;

FIG. 9 is a sectional view of the operation section;

FIGS. 10 and 11 are sectional views which show the internal mechanism of the operation section;

FIG. 12 is a sectional view showing a connection portion between the operation section and ocular section;

FIG.13 is a cross sectional view of a casing; and

FIG. 14 is a view explaining the function of the casing.

DETAILED DESCRIPTION OF THE PREFERRED EMBODIMENT

An embodiment of the invention may now be described with reference to FIGS. 2 to 14.

Figure 1:
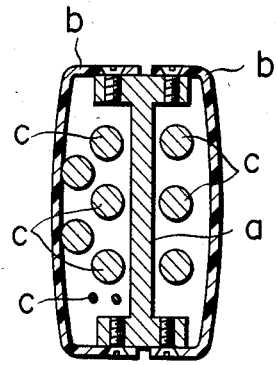
FIG. 1 is a cross sectional view of the operation section of a prior art endoscope.
Figure 2:
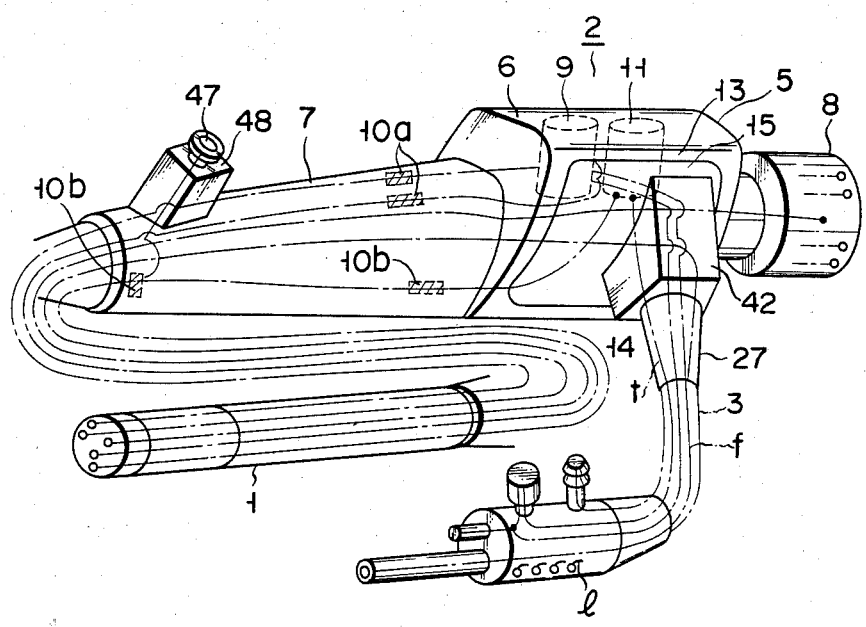
Figure 3:
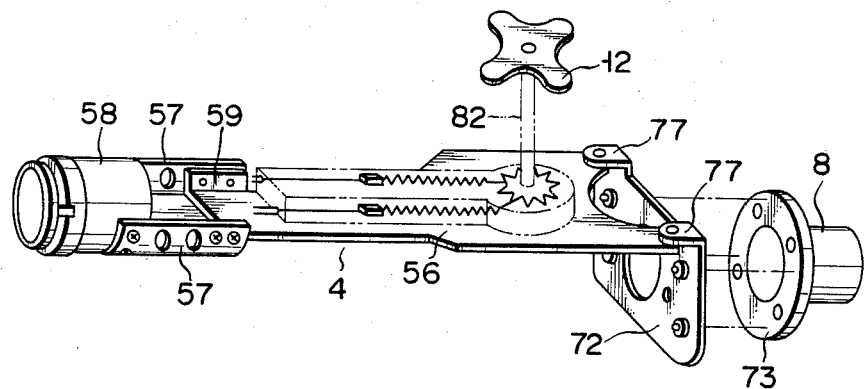

FIG. 2 schematically shows an entire endoscope. This endoscope is comprised of an insertion section 1, an operation section 2 and a light guide cable section 3. The operation section 2 is comprised of a main body 4 as shown in FIG. 3, and a casing 5 (FIGS. 2 and 9) consisting of synthetic resin and so arranged as to cover and contain the main body 4. Further, the casing 5 is divided into two parts, one of which is a casing body 6 made substantially rectangular and shaped like a hollow box and the other of which is a cylindrical gripping cover 7. Those two parts are joined together in such a manner that their hollow portions are allowed to come into contact with each other. The casing body 6 is provided with an ocular portion 8, an air/water feed control element 9, suction control element 11 and a bending operation knob 12 (FIG. 3). Note here that the reference numeral 10a in FIG. 2 denotes an intermediate coupling portion of an air/water feeding tube while the reference numeral 10b denotes an intermediate coupling portion of a suction tube 54 as later described. These intermediate coupling portions 10a, and 10b are disposed within the gripping cover 7. Further, an inclined face 13 is formed on the portion of the casing body 6 opposite to the portion where the bending operation knob 12 is provided. This inclined face 13 is provided with an opening portion 14 in such a manner that this portion 14 is opposed to the main body 4 of the operation section. The opening portion 14 is attached with a casing cover 15, that is, a lid membe 15, which consists of synthetic resin in such a manner that the opening is closed by the lid member 15. To this casing lid member 15, there is connected a base end of the above-mentioned light guide cable 3.

The joining structure wherein the casing lid member 15 is joined or coupled to the casing body 6, as well as the connecting structure wherein the light guide cable 3 is connected to the main body 4 of the operation section 2, may now be described in detail, with reference to FIGS. 5 and 6. A fixing metal fitting 17 is provided on the surface of the main body 4 in opposition to the opening portion 14. This fixing metal fitting 17 is formed or prepared by fabricating, i.e., by pressing a thin metal plate, such as that which has a Japanese Industrial Standard of, e.g., C 1720P, C 5211P, C 2680P, C 2800P, A 5052P, SPCC, SUS 304CP, etc., and is comprised of a top plate portion 18 and three support leg portions 19 made integral with the top plate portion 18 and bent from the same. Further, a bent portion 19a is formed on the lower end portion of each of the three support leg portions 19 and is formed with an attaching hole 19b, through which a fastening screw 20 is idly inserted via a spring washer 20a. The fixing metal fitting 17 is attached to the main body 4 of the operation section by means of the fastening screw 20. Accordingly, the top plate portion 18 of the fixing metal fitting 17 and upper portions of the support leg portions 19 are allowed to protrude from the opening portion 14 of the casing body 6. The top plate portion 18 and support leg portions 19 thus protruded are formed with attaching holes 21. To this fixing metal fitting 17 there is connected a base end portion of the light guide cable 3. That is, the light guide cable 3 is comprised of a flexible tube 22 used to have equipped therein elongate members such as a light guide fiber f, a fluid transport pipe t and an electric signal wire l, and a mouthpiece pipe 23 fitted to an end portion of this flexible tube 22. A base end portion of the mouthpiece pipe 23 is formed with a notched portion 24, which is formed with screw holes 25 arranged to oppose said attaching holes 21 of the fixing metal fitting 17. Thus, the fixing metal fitting 17 and the base end portion of the mouthpiece pipe 23 are integrally fixed to each other by screwing into the screw holes 25 the fixing screws 26 passing through the attaching holes 21. Further, onto the base end portion of the flexible tube 22 there is fitted a break preventive rubber tube 27 whose open end has a mouthpiece 28 screwed thereinto and thus joined thereto. Further, a base end portion of a fastening ring 29 is screwed into and joined and fixed to this mouthpiece 28. The fastening ring 29 is allowed to protrude from the end face of the break preventive rubber tube 27, the protruded portion thereof being formed with a first annular groove 30 on its inner peripheral surface and a second annular groove 31 on its outer peripheral surface. The first and second annular grooves 30 and 31 are formed in such a manner that they adjoin to each other in the axial direction of the light guide cable section 3. The first and second annular grooves 30 and 31 have received therein resilient seal members 32 and 33 consisting of O-ring, respectively. A stepped portion 34 is provided on the outer peripheral surface of the portion of the fastening ring 29 located between the first and second annular grooves 30 and 31; while, on the other hand, an internally threaded portion 35 is formed on the inner peripheral surface of the fastening ring corresponding to the second annular groove 31. This internally threaded portion 35 is screwed onto an externally threaded portion 36 provided on the outer peripheral surface of the mouthpiece pipe 23. Further, the base end face of the fastening ring 29 is integrally provided with a fastening annular portion 37 shaped like a wedged in section, in such a way that this portion is engaged with the casing lid member 15.

Further, the opening portion 14 provided with reference to the inclined face 13 of the casing body 6 is formed in a rectangular shape and is provided, on its inner peripheral edge, with an inclined pressure receiving portion 38. The casing lid member 15 is made rectangular, in such a manner that it closes the opening portion 14; and is provided, on its outer peripheral edge, with an inclined pressure application portion 39, which is to be joined to the inclined pressure receiving portion 38. The casing lid member 15 is also formed, along its outer peripheral edge, with a protruded portion 40 at a position inward of the inclined pressing portion 39. On the outer side of the protruded portion 40, there is fitted a resilient seal member 41 consisting of O-ring which is intended to seal, on a watertight basis, the portion between the outer side of the protruded portion and the inner peripheral surface of the casing body 6. On the outer surface of the casing lid member 15, there is integrally protruded a square hollow member 42 which covers the fixing metal fitting 17. A tip end portion of the fitting hollow member 42 is provided with a circular fitting portion 43 fitted onto the outer periphery of the fastening ring 29, and an opening end of this fitting portion 43 is formed with a fitting step portion 44 opposing the stepped portion 34 of the fastening ring 29. An inner peripheral protrusion portion 45 is provided on a portion, opposing a part of the fastening annular portion 37, of the inner peripheral surface of the fitting square hollow member 42. This inner peripheral protrusion portion 45 is formed with an engaging notched portion 46 which is to be brought into engagement with the fastening annular portion 37.

The method of connecting, for assembly, the light guide cable 3 to the main body 4 of the operation section fixed to the casing 5 may be described as follows. The fixing metal fitting 17 is inserted into the casing body 6 from the opening portion 14 thereof and the support leg portions 19 are fastened and secured to the main body 4 by means of the fixing screws 20. In this case, since the attaching holes 19b of the support leg portions 19 are each made large enough (in diameter) to permit the fixing screw 20 to idly pass therethrough, it is possible to fix the fixing metal fitting 17 to the main body 4 of the operation section on an adjustable basis. Thereafter, the base end portion of the mouthpiece pipe 23 provided with reference to the flexible tube 22 of the light guide cable 3 is positioned with respect to the top plate portion 18, whereby the mouthpiece pipe 23 and the fixing metal fitting 17 are integrally attached to each other by means of the fixing screws 26. In this case as well, since the fixing metal fitting 17 is formed of a thin metal plate or sheet, the positioning of the mouthpiece pipe 23 can be adjusted by elastically deforming the fixing metal fitting 17. Thus, it is also possible to position the metal fitting 17 relative to the fitting square hollow member 42 of the casing lid member 15, which will be described later. On the other hand, after the resilient seal member 41 is fitted onto the protruded portion 40 of the casing lid member 15, the fitting square hollow member 42 of the casing lid member 15 covers the flexible tube 22 of the light guide cable 3. Then, the casing lid member 15 is moved toward the casing body 6; and, while the fixing metal fitting 17 is enclosed by the hollow member 42, the inclined pressing portion 39 of the casing lid member 15 is allowed to abut against the inclined pressure receiving portion 38 of the casing body 6, thereby closing the opening portion 14. Thereafter, the fastening ring 29 fitted with the resilient seal members 32 and 33, and the break preventive rubber tube 27 integrally joined thereto, cover the flexible tube 22 of the light guide cable 3, thereafter to screw the internally threaded portion 35 onto the externally threaded portion 36 of the mouthpiece pipe 23 of the flexible tube 22, thereby to fasten the fastening ring onto the same. In this case, since the axis 15a of the light guide cable 3 is eccentric from the axis 42a of the fitting square hollow member 42, by α, the fastening of the fastening ring 29 causes the resilient seal member 33 to exert a force acting in a direction perpendicular to the axis 15a, namely in the direction of arrow A. Further, since the fastening annular portion 37 of the fastening ring 29 is engaged with the engaging notched portion 46 of the inner peripheral protrusion 45 of the fitting square hollow member 42, the fastening of the fastening ring 29 causes a force acting in the direction indicated by arrow P to be applied to the inner peripheral protrusion 45. As a consequence, the casing lid member 15 and the casing body 6 are adhered or bonded to each other by a joining of the inclined pressing portion 39 to the inclined pressure receiving portion 38. Although, in this case, the resilient seal member 33 has its body biased by the fastening of the fastening ring 29, the sealing between the fastening ring 29 and the casing lid member 15 is ensured, even when such resilient seal member has its body maximally biased to a value great enough to permit the creation of a clearance therebetween. Thus, the sealing of the fastening ring 29 to the mouthpiece pipe 23 is completely achieved by the resilient seal member 32, on a watertight basis. On the other hand, the sealing of the casing body 6 to the casing lid member 15 is accomplished by means of the resilient seal member 41, on a watertight basis.

Meanwhile, the above-mentioned gripping cover 7 has an outer diameter and a length which are suitable for gripping by an examiner using only one hand. On the side face of an end portion of the cover 7 located on the side of the insertion section 1, there is integrally formed an attaching hollow portion 48 used to mount a channel mouthpiece 47 thereto as shown in FIGS. 7 and 8. That is, the channel mouthpiece 47 is removably inserted from outside and fitted into the attaching hollow portion 48 and is fixed thereto by means of a pair of attaching screws 51, as shown in FIG. 7. Further, as shown in FIG. 8, the channel mouthpiece 47 is connected to one end of a three-way joint 52. To one of the remaining ends of the three-way tube, there is connected a channel tube 53, and a suction tube 54 is connected to the other of said remaining ends. This provides the above-mentioned intermediate coupling portion 10b wherein the channel tube 53 and the suction tube 54 are respectively connected to the ends of the three-way joint 52.

Also, the main body 4 of the operation section disposed within the casing 5 as shown in FIG. 3, is comprised of a plurality of members; or, as in this embodiment; is comprised of a base plate 56 made of metal, a pair of frames 57 and a cylindrical member 58. More specifically, a pair of bent piece portions 59 are provided on an end portion of the metallic base plate 56 located on the side of the insertion section 1. Further, a pair of said frames 57 are screwed and connected, at one end, to the bent piece portions 59, respectively, and, at the other end, to the side surface of the cylindrical member 58. The base plate 56 is so disposed as to extend through the casing body 6 and the gripping cover 7. The paired frames are disposed within the gripping cover 7, and the cylindrical member 58 is disposed in such a manner as to extend and project from a tip end opening portion of the gripping cover 7. To the cylindrical member 58, the said three-way joint 52 is attached and stabilized by means of setscrews 61, as shown in FIG. 8. Further, a base end portion 62 of the flexible tube extending from the insertion section 1 is connected, by means of a check ring 63, to an extended tip end portion of the cylindrical member 58. Further, a break preventive member 65 consisting of resilient material having a relatively high rigidity is connected to the cylindrical member 58 through a connecting pipe 64. Further, a cylindrical watertight cover 66 is fitted onto the outer periphery of the cylindrical member 58 and is partially allowed to enter the opening end of the gripping cover 7 and is connected thereto on a watertight basis. The other end of the watertight cover 66 is joined to an end face of the break preventive member 65. Ring-like resilient packings 67 are interposed between the joining portions of the watertight cover 66 and the gripping cover 7, between the joining portions of the watertight cover 66 and the cylindrical member 58 located on the side of the insertion section 1, and between the cylindrical member 58 and a base end portion of the insertion section 1, respectively, so as to ensure the watertightness therebetween.

Meanwhile, on the inner peripheral surface of an opening portion of the gripping cover 7 located on the side of the insertion section 1, a receiving portion 68 is formed, which portion 68 projects toward the central axis thereof, over the entire inner peripheral surface of said opening portion, as shown in FIG. 8. Against this receiving portion 68, a pair of nut-like juxtaposed fastening members 71 are abutted, being screwed onto an external thread 69 formed on the outer peripheral surface of the cylindrical member 58. When these fastening members 71 are advanced toward the side of the gripping cover 7, it is possible to press this gripping cover and at the same time the main body 4 of the operation section is pulled as a reaction of this pressing operation.

On the other hand, the other end of the main body 4 of the operation section 2, i.e., the end of the base plate 56 located on the side of the ocular portion 8, is attached and fixed, for example, to a side wall 74 of the casing body 6 by means of a pair of members, such as metallic members 72 and 73 as shown in FIGS. 3 and 12. Specifically, the side wall 74 is sandwiched between the paired metallic members 72, 73 and is fastened and fixed therebetween by means of setscrews 75, each passing through these three members, and by mean of nuts 76.

The inner metallic member 72 has a piece 77 formed on one side edge thereof, which piece 77 is screwed onto the base plate 56. Further, the parts of the ocular portion 8 are assembled on the outer metallic member 73, as shown in FIG. 12.

The casing body 6 of the casing 5 and the gripping cover 7 are connected to each other in a manner such as that shown in FIG. 9. That is, the casing body 6 is formed with a projection 79 which projects toward the side of the gripping cover 7 from a joining end face 78 of the casing body 6 and which has a configuration corresponding to that of the opening portion of the grippint cover 7. Further, said projection 79 is so arranged as to be fitted into the opening end of the gripping cover 7. Further, an inner peripheral surface of the opening end portion of the gripping cover 7 fitted with the projection 79 is made large in diameter correspondingly to the thickness of the projection 79, whereby a step portion 80 is formed. A projection portion 80a allowed to project toward the casing body 6 is formed on a tip end of a rising wall surface of this step portion 80 while, on a tip end of the projection 79 as well, a projection portion 79a is so formed as to corresponding to the projection portion 80a. The projection portions 79a and 80a are each formed with an inclined surface at the side of the bottom surface of the step portion 80, and a resilient packing 81 shaped like a ring is fitted into a space portion thus enclosed by those surfaces.

The base plate 56 of the main body 4 of the operation section has a bending operation mechanism mounted thereon, as shown in FIG. 9. On the upper surface of one end portion of the base plate 56 located within the casing body 6, there is provided a fixing portion 82a of a shaft 82 provided projecting from the base plate. An inner sleeve 83 and an outer sleeve 84 are rotatably fitted onto the shaft 82. The sleeves 83, 84 are respectively engaged at one of their side ends with a pair of sprockets 85 (only one of which is shown) disposed at upper and lower positions in the axial direction of the shaft 82, in such a manner as to be rotatable thereabout; and are allowed, at their other side ends, to project from the casing body 6, being respectively connected to the above-mentioned bending operation knobs 12 (only one of which is shown in FIG. 3). Further, on the upper surface of the other end of the base plate 56 allowed to project into the gripping cover 7, a partitioning member 86 which U-shaped in cross section is attached and fixed to the base plate 56 (longitudinally thereof) by means of a fixing plate 87, through its intermediate bottom portion. Outside each side wall of the partitioning member 86, a passage 89 is defined by a defining wall 88, in such a manner that the resultant passages 89 are arranged at upper and lower stages, with the partitioning member interposed therebetween. The defining wall 88 is divided into two parts, one being an inner defining wall 88a and the other being an outer defining wall 88b, in the widthwise direction of the passage 89. The inner and outer defining walls 88a and 88b are supported by and fixed to support portions 90a and 90 erected on the base plate 56, at their midway positions taken in their longitudinal directions and at their ends located on the side of the sprockets 85.

An attaching plate 91 is erected on the upper surface of the end portion of the partitioning wall member 86 located on the side opposite to that at which the sprockets 85 are disposed. To this attaching plate 91, there is joined and fixed a flat-plate like retaining member 92 having a width greater than that of the partitioning wall member 86. On both ends of this retaining member 92 taken in the widthwise direction thereof, sets of notches 93, which sets each consist of two notches, are formed correspondingly to the passages 89, respectively. At the notch 93, there is provided a hollow cylindrical regulating member 94 formed with a step portion 94a made smaller in diameter at a midway position taken in the axial direction thereof, in a state wherein the step portion 94a is engaged with the notch 93 in such a manner that this regulating member 94 is thereby prevented from being moved in the axial direction thereof. This regulating member 94 is held in place in such a manner that the disengagement thereof from the notch 93 is prevented by the abutment of an end portion of the outer defining wall member 88b against the peripheral surface of the regulating member 94. Further, into the hollow cylindrical regulating member 94, a base end portion consisting of a flexible wire guide pipe 95 comprised of a coil of a close winding or the like is inserted into the insertion section 1 throughout the entire length thereof, whereby said base end portion is fixed by brazing to the regulating member 94, by the use of a brazing material member 96a. A wire 96 is inserted through the wire guide pipe 95. This wire is connected and fixed at its tip end to a top (not shown) constituting the bending portion, and is lead into the passage 89 at its base end side. A connecting member 97 is connected to the base end of the wire 96 guided into and through the passage 89. An end portion of a chain 98 engaged at its midway position with the above-mentioned sprocket 85 is connected to the connecting member 97. Further, on the connecting member 97, there is planted or provided an abutment member 99 in such a manner that the member 99 intersects the axial line of the wire 96 at right angles thereto. A part of this abutment member 99 is allowed to project toward an outside of the base plate 56 taken in the widthwise direction thereof. The outer peripheral surface of this projected portion of the abutment member is formed into an inclined surface 100 defining an acute angle with an end face thereof.

On the other hand, a wall portion 101 formed by bending a part of the base plate 56 or a separate member into the shape of the letter U-shape is provided between the first and second support portions 90a, 90 erected on the base plate 56. A support hole 102 is formed in one way portion of this wall portion 101 located along the widthwise direction of the base plate 56. On this support hole 102, there is rotatably supported a screw 103 having a receiving portion 103c between its threaded portion 103a and its head portion 103b, through this receiving portion 103c. The screw 103 is provided in such a manner that its axial line is made parallel to the axial line of the wire 96 and is located at a position, on the outside of the base plate 56 taken in the widthwise direction thereof, which is more outward of this plate than the axial line of the wire 96. A terminal end of the threaded portion 103a is engaged with a support hole 104 formed in the second support portion 90. A stopper 105 is screwed onto the threaded portion 103a of the screw 103 and has a height slightly lower than the height of the passage 89. As a result, when the screw 103 is allowed to rotate about its axis, the upper surface of the stopper 105 is allowed to abut against an upper wall surface of the passage 89 and is thereby prevented from being rotated in such a way as to be moved forwards and backwards through the passage 89. Here, it should be noted that the passage 89 corresponding to a portion wherein the screw 103 is provided is defined by the above-mentioned defining wall 88b. On the side of the stopper 105 directed toward the partitioning wall member 86, an inclined surface 106 having an angle of inclination corresponding to the inclined surface 100 of the abutment member 99 is formed. By abutment of the inclined surface 100 of the abutment member 99 against the inclined surface 106 of the stopper 105, the travel of the wire 96, i.e., the maximum bending angle of the bending portion defined in the rightward and leftward directions, as well as in the upward and downward directions, is limited.

The head portion 103b of the screw 103 is formed with an engaging bore 107 allowed to pass therethrough, in the radial direction thereof. An engaging stopper spring 108 prepared by bending a wire into a waveform configuration is engaged at one end with said engaging bore 107. Further, the engaging stopper spring 108 is pressed at the other end against the first support portion 90a in a state wherein it is kept compressed. Accordingly, the screw 103 is prevented by the engaging stopper spring 108 from being rotated about its axis, and an end face of the head portion 103b is pressed due to the restoring force of the engaging stopper spring 108 against a side face of the wall portion 101, whereby the head portion 103b is prevented from being moved in a direction in which it is escaped from, or spaced away from, the support hole 102.

In the bending operation mechanism having the foregoing construction, when the sprocket 85 is rotated by the bending operation knob 12 for the purpose of bending the bending portion of the insertion section 1, and the chain 98 is thus allowed to travel, the wire 96 located in one of said passages 89 in the widthwise direction of the base plate 56 is pulled, while the wire 96 located in the other of said passages 89 in a similar direction is pushed. Accordingly, the bending portion is bent toward the side of the wire 96 pulled. When the wire 96 is further pulled, the inclined surface 100 of the abutment member 99 provided to the connecting member 97 connecting the wire 96 at the base end thereof to the chain 98 is brought into abutting engagement with the inclined surface 106 of the stopper 105. This makes it impossible to pull the wire 96 any further. Thus, the maximum bending angle of the bending portion is defined by the stopper 105. Further, when the abutment member 99 is allowed to abut against the stopper 105, the screw 103 is pressed onto the side face of the second support portion 90 through the stopper 105. At this time, however; in this screw 103, the end face of the head portion 103b thereof is allowed to abut against the side face of the wall portion 101, whereby the screw 103 is prevented from being axially moved, along with the stopper 105. As a result, the possibility that the maximum bending angle of the bending portion would become greater than an initial preset angle may be eliminated.

The following procedural operations should be conducted for the purpose of changing the maximum bending angle of the bending portion. The engaging stopper spring 108 provided, in a state wherein it is compressed, between the first support portion 90a and the engaging bore 107 of the head portion 103b of the screw 103 is dismounted by being further compressed. Next, the screw 103 is rotated, whereby the stopper 105 is displaced toward the second support portion 90. Thereafter, the bending portion is bent until it has a predetermined bending angle, by rotation of the bending operation knob 12. Then, while the bending operation knob 12 is kept thus rotated, the screw 103 is rotated in the opposite direction to that in which the preceding rotation thereof was made, until the inclined surface 106 of the stopper 105 abuts against the inclined surface 100 of the abutment member 99. Subsequently, the engaging stopper spring 108 is again mounted between the first support portion 90a and the engaging bore 107 of the head portion 103b of the screw 103, whereby the stopper 105 is fixed to a predetermined position through the screw 103. Thus, the maximum bending angle of the bending portion is set by the stopper 105.

Although a slight rotation of the screw 103 from a prescribed position thereof is necessary, to cause the end portion of the engaging stopper spring 108 to come into engagement with the engaging bore 107, the stopper 105 is almost unmoved, due to such slight rotation of the screw 103, only if the pitch of the screw 103 is made sufficiently small. Thus, there is no positive effect on the maximum bending angle of the bending portion.

Figure 4:
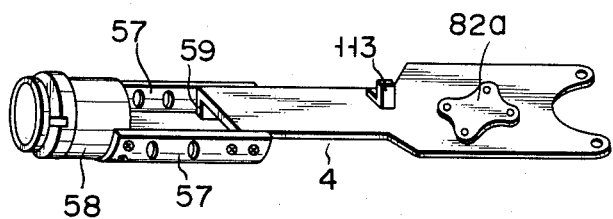
Figure 10:
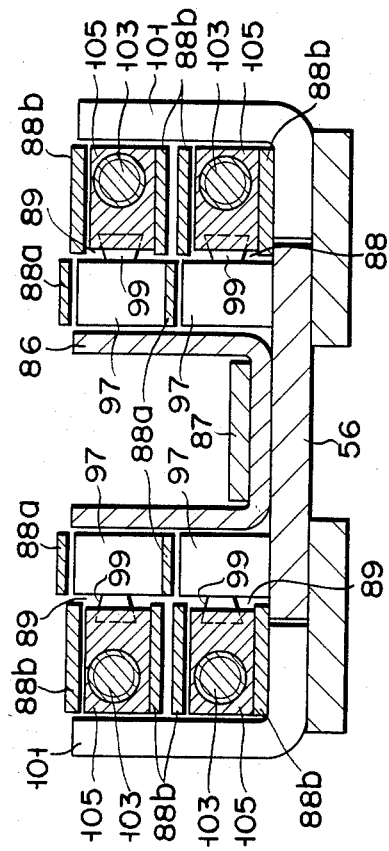
Figure 11:
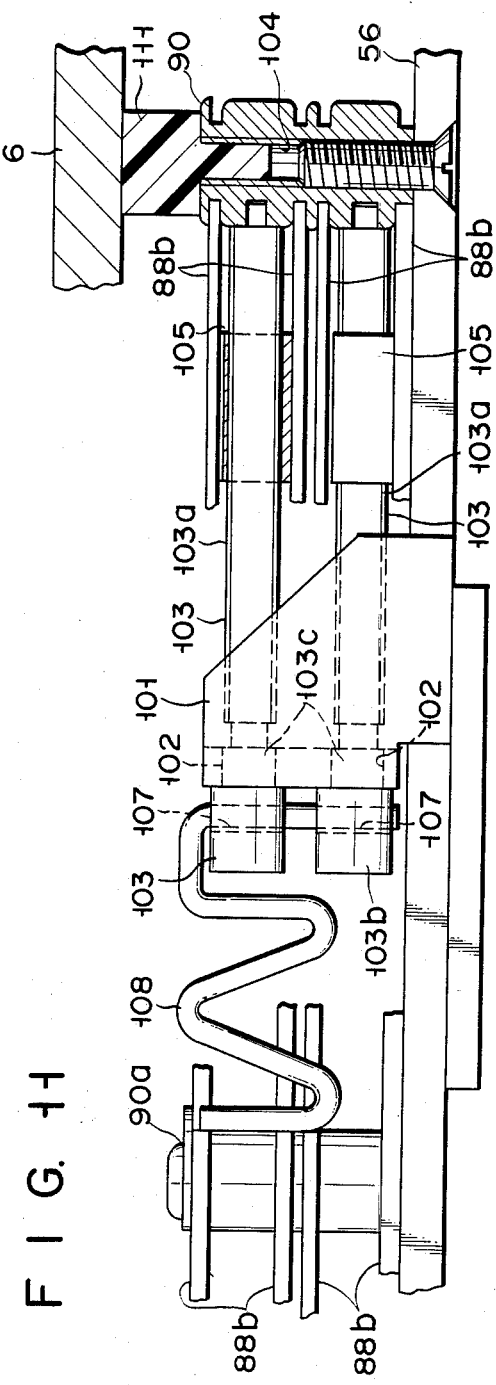
Figure 13:
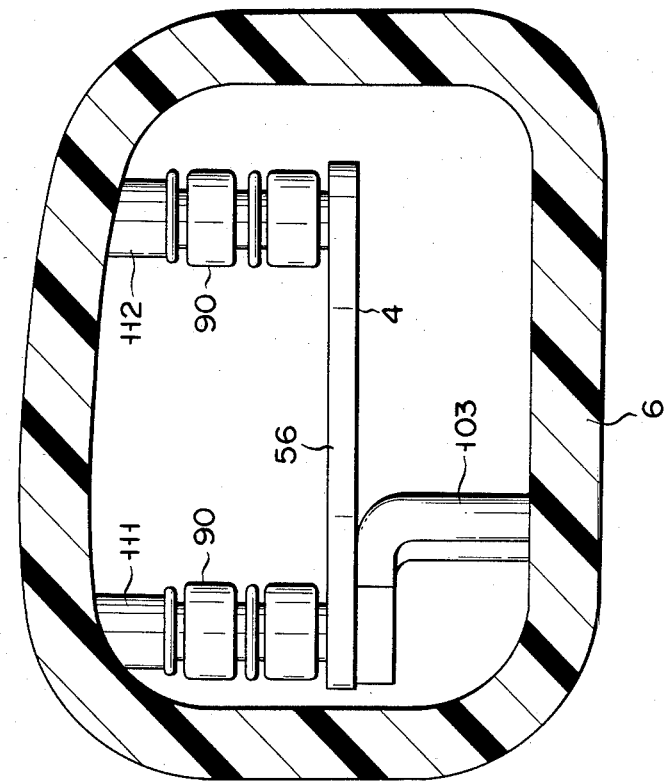

Meanwhile, flexure preventive stopper members 111, 112 are mounted upon protruded tip ends of the support portions 90, respectively, as shown in FIGS. 11 and 13. The flexure preventive stopper members 111, 112 are each made of a synthetic resinous material and are mounted in such a manner that their external threaded portions formed on their one-side end portions are screwed into the threaded bores 104 formed in the support portions 90. The other side ends of these flexure preventive stopper members 111, 112 are allowed to abut against the inner wall surface of the casing 5; or, in this case, against the inner wall surface of the casing body 6. As shown in FIG. 4, a stopper piece 113 serving as a separate flexure preventive stopper member is screwed and fixed to the base plate 56 at a position thereof which is opposite to that at which the flexure preventive stopper members 111, 112 are fixed thereto. As shown in FIG. 13, this stopper piece 113 abuts against the inner wall surface (i.e., the inner wall surface opposite to that against which the flexure preventive stopper members 111, 112 abut) of the casing body 6. It should be noted here that, preferably, the flexure preventive stopper members 111, 112 and the stopper piece 113 are disposed substantially on flat planes intersecting the surface of the base plate 56 at right angles thereto, as shown in FIG. 13. That is, since the flexure preventive stopper members 111, 112 and the stopper piece 113 are provided on the sides of the main body 4 of the operation section at which the same is flexed and swollen, for example, at the time of the bending operation, in such a manner that they are allowed at all times to abut against the inner wall surfaces of the casing body 6, the main body 4, especially the base plate 56, is prevented from being flexed at the time of, for example, the bending operation, even when it tends to be flexed. The prevention of such flexure is completely achieved by the stopper members 111, 112 and the stopper piece 113, although this prevention is also due to the fact that a pulling force acts upon the main body 4 of the operation section, as later described. This also produces the effect of making it possible to construct the main body 4 of the operation section in such a way that the same is made thinner and more compact. Further, only a very small stress is applied to the stopper members 111, 112 and the stopper piece 113 due to their abutment against the casing body 4, and no unnecessary concentrated stress is applied thereto. Here, it should be noted that the flexure preventive stopper members 111, 112 and the stopper piece 113 are not required to be kept in constant abutment against the inner wall of the casing body 6 in a state wherein they are cohered to this inner wall, but may be spaced therefrom to such an extent that, when the main body 4 has been flexed slightly, they may abut against said inner wall.

Thus, the assembling structure of the operation section 2 is so disposed that the hollow box casing body 6 and the cylindrical gripping cover 7 are joined together to form the cylindrical casing 5 as a whole; the main body 4 is inserted and disposed within said casing 5; and the ends of the casing 5 are supported by the main body 4 of the operation section, in such a manner as to afford a pulling force to pull the main body 4. Thus, the end of the main body 4 of the operation section 2 located on the side of the ocular portion 8 is attached and fixed to the side wall 74 of the casing body 6 by utilizing said pair of metallic members 72, 73. The cylindrical member 58 of the end portion, located on the side of the insertion section 1, of the main body 4 of the operation section is supported in a state wherein the fastening member 71 is pressed against the receiving portion 68 of the gripping cover 7, and the main body 4 of the operation section receives a pulling force while, on the other hand, the casing 5 receives a compression force as a reaction. Further, the resilient packing 81 disposed between the casing body 6 and the gripping cover 7 is compressed, whereby watertightness is ensured therebetween.

Meanwhile, the casing 5 resists the flexure, buckling and bending forces resulting from its being compressed. However, since the casing 5 is designed to occupy the outermost position of the operation section 2, in particular, and is formed into a hollow box and into a cylinder, the casing 5 has a large section modulus, even when its thickness is reduced. Accordingly, it is possible to make the casing 5 fine and light; and, at the same time, this casing can have a high resistance to the compression and the bending force. Since, on the other hand, the main body 4 of the operation section is so constructed that it receives a pulling force, this main body can be made thin and fine by being formed of metal or the like. That is, since the main body 4 of the operation section can be so designed as to have a sufficiently high mechanical strength against the pulling force, even when it is made thin and fine, this main body can be formed into a compact structure. Moreover, since the main body 4 has a pulling stress at all times, it offsets the compression force acting upon the operation section 2. Further, since the pulling stress is at all times afforded to the main body 4 of the operation section, this main body 4 has a higher resistance to the bending force than in the case where the main body 4 has no pulling stress.

Figure 14:
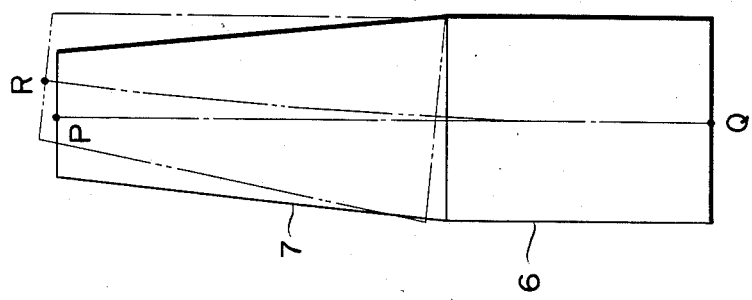

Still further, where the casing body 6 and the gripping cover 7 tend to be separated from one another at the face of the abutment therebetween; and, thus, the casing tends to be bent at this face, as shown in FIG. 14 by two-dot chain lines, the main body 4 of the operation section must be bent and increased in length (QP<QR). However; since, as mentioned above, the bending and the increase in length of the main body 4 of the operation section are lessened, the variation likely to occur in the casing is suppressed. Accordingly, the bending of the casing at the position of abutment between the casing body 6 and the gripping cover 7 is also prevented. For the above-mentioned reasons, the operation section 2 can be not only constructed such that it has a sufficiently high resistance to the pulling force and is made fine and light in weight, but can also have a sufficiently high resistance to the compression and bending force as well. In the prior art structure, when an attempt is made to obtain a sufficiently high resistance to, or mechanical strength against, the compression and bending force, the operation section 2 becomes bulky or large in mass and heavy and besides has an excessive strength against the pulling force thus to have a uselessness in that regard. In the above-mentioned structure of the present invention, however, the distribution of the sectional area and weight involved is made such that the portions of the main body 4 of the operation section where inconvenience arises to obtain a strength against the compression and bending force are reduced in sectional area and weight and that the sectional area and weight of the outermost casing member is increased by that extent. Thus, according to the structure of the present invention, the operation section 2, while the strengths thereof against the pulling, compression and bending forces are being made optimum, is made fine and light in weight and also has a sufficiently high strength.

Moreover, in the assembling structure mentioned above, when the casing body 6 is dismounted, the connecting or joining portions contained therein are exposed, with the result that the efficiency with which the assembling operation is carried out increases. Also, since the sealing portion between the casing body 6 and the gripping cover 7 may easily be formed as a simple ring-like joining portion, the sealing structure at that sealing portion is simple and permits a reliable sealing between both. In this regard, it should also be mentioned that the mounting of the casing body 6 to the gripping cover 7 is achieved by the pressing of one against the other, by means of the fastening member, and does not require any superfluous through-hole, such as a hole for permitting the passage therethrough of a setscrew or the like, with the result that the sealability therebetween is increased. In addition, since no abrasion occurs, due to the eccentricity of the through-hole relative to the setscrew, or vice versa, it is easy to use a synthetic resinous material; and, at the same time, the manufacturing cost involved is decreased, if the molding technique is applied.

Further, since, in the above-mentioned structure, the main body 4 of the operation section is stabilized in such a way that the side wall 74 of the casing body 6 is sandwiched between the metallic members 72, 73, a pair of members relatively large in area, this stabilization is achieved on a firm and reliable basis. Simultaneously, the concentration of a stress onto the casing body 6 is thus lessened with the result that the durability thereof is increased.

Still further, at the time of bending operation, the compression and bending forces are applied to the main body 4 of the operation section between the portion of fixing the base end of the bending operation wire guide pipe 95 and the portion of fixing the bending wire advancing and retreating means. However, since such compression and bending forces are allowed to act on that portion of main body between both which has a pulling force applied in advance, the compression force is offset by this pulling force while the bending force is resisted by this pulling force to a high degree.

As stated above, according to the present invention, it is possible to make the operation section light in weight while providing a structure therefor which has sufficient mechanical strength to resist compression and bending foces, having high durability. In addition, since the assembling operability for the operation section is high the sealability therefor can also be enhanced, and the manufacturing cost therefor is also reduced. These are additional advantages or effects of the present invention.

What is claimed is:

1. An endoscope comprising:
    an operating mechanism;
    a main body of an operation section holding said operating mechanism and having a base end and a protruded portioon extending in the opposite direction fron the base end; and
    a casing within which said main body of the operation section is enclosed,
    wherein said casing includes:
    a hollow box-like casing body with one of its end portions serving to stabilize said base end of said main body of the operation section and its other end portion having an opening portion permitting said protruded portion of said main body of the operation section to be extended extrinsically of said casing; and
    a cylindrical gripping cover having an end portion abutting against said other end portion of said casing body and covering said protruded portion of said main body of the operation section;
    and wherein said main body of the operating section includes:
    a fastening member connected to said protruded portion of said main body of the operation section and engaged with said gripping cover, whereby said fastening member acts to urge said gripping cover toward said casing body and, at the same time, to urge said casing body toward said gripping cover, thereby pressing said end portion of said gripping cover and said other end portion of said casing body against each other.

2. An endoscope according to claim 1, wherein said protruded portion of said main body of the operation section has a cylindrical member with an external thread on its outer peripheral surface; said gripping cover has a protruded portion on its inner peripheral surface; and said fastening member has a screw member brought into screwing engagement with said external thread and having an end face allowed to abut against an end face of said protruded portion of said gripping cover.

3. An endoscope according to claim 2, wherein said screw member has a pair of nuts juxtaposed with respect to each other and having one-side end faces allowed to abut against an end face of said protruded portion of said gripping cover.

4. An endoscope according to claim 3, wherein said end portion of said gripping cover has an annular stepped portion; said other end of said casing body has an annular protrusion so protruded as to face said stepped portion of said gripping cover; and a resilient packing shaped like a ring is further provided between said annular stepped portion and annular protrusion for the purpose of providing a sealing between said gripping cover and said casing body, by being pressed by said annular stepped portion and annular protrusion.

5. An endoscope according to claim 1, wherein said casing body is formed of a synthetic resin; and a pair of metallic plates are further provided for sandwiching a part of said casing body, said main body of the operation section being attached to one of said pair of metallic plates.

6. An endoscope according to claim 5, wherein an ocular portion is further provided and this ocular portion is fixed to the other of said pair of metallic plates.

7. An endoscope according to claim 1, wherein said main body of said operation section has a metallic base plate extending from said casing body to said gripping cover, said metallic base plate having at least one stopper projectively provided on the side thereof at which said base plate is flexed and adapted to prevent the flexure of said base plate by abutment of its tip end against said casing body.

* * * * *